(12) United States Patent
Tsai et al.

(10) Patent No.: US 6,171,831 B1
(45) Date of Patent: Jan. 9, 2001

(54) **METHOD FOR THE PRODUCTION OF ITACONIC ACID USING *ASPERGILLUS TERREUS* SOLID STATE FERMENTATION**

(75) Inventors: Ying-Chieh Tsai; Min-Chang Huang; Shuen-Fuh Lin; Yuan-Chi Su, all of Taipei (TW)

(73) Assignee: National Science Council, Taipei (TW)

( * ) Notice: Under 35 U.S.C. 154(b), the term of this patent shall be extended for 0 days.

(21) Appl. No.: 09/510,449

(22) Filed: Feb. 22, 2000

Related U.S. Application Data

(63) Continuation of application No. 08/982,368, filed on Dec. 2, 1997, now abandoned.

(51) Int. Cl.⁷ ....................................................... C12P 7/44
(52) U.S. Cl. ...................... 435/142; 435/254.3; 435/145
(58) Field of Search .................................... 635/145, 142, 635/911, 254.3

(56) References Cited

PUBLICATIONS

Oriol et al., Journal of Fermentation Technology, vol. 66, No. 1, pp. 57 to 62.*
Kautola et al., Biotechnol. Lett., vol. 7, pp. 167–172, 1985.*
Kautola et al., Biotechnol. Lett., vol. 11, pp. 313–318, 1989.*

* cited by examiner

*Primary Examiner*—Irene Marx
(74) *Attorney, Agent, or Firm*—Bucknam and Archer

(57) ABSTRACT

The method to produce itaconic acid is a solid-state fermentation method. Sugarcane pressmud or peeled sugarcane pressmud is the support used to adsorb liquid medium for the production of itaconic acid by an *Aspergillus terreus* mutant strain. This mutant strain was derived from *Aspergillus terreus* ATCC 10020 by successive mutation. Beside the remaining sucrose in the sugarcane pressmud, other carbon source can be added, i.e. glucose, fructose, sucrose, or starch hydrolysate. Appropriate amounts of nitrogen source, such as ammonium nitrate, or ammonium sulfate are added. Mineral salts, such as potassium dihydrogen phosphate, magnesium sulfate, calcium sulfate, ferric chloride, zinc sulfate, and copper sulfate can be added to the medium. The suitable amount of liquid medium that can be added to the support is 4 to 6 times its dry weight for the sugarcane pressmud and 8 to 14 times its dry weight for the peeled sugarcane pressmud. The optimal pH of the medium is between 2.0–3.0. The fermentation temperature is between 30–40 degrees centigrade.

1 Claim, 3 Drawing Sheets

METHOD FOR THE PRODUCTION OF ITACONIC ACID USING *ASPERGILLUS TERREUS* SOLID STATE FERMENTATION

REFERENCE TO RELATED APPLICATION

This application is a continuation of application Ser. No. 08/982,368, filed Dec. 2, 1997, now abandoned.

FIELD OF THE INVENTION

Itaconic acid is an unsaturated organic acid. Its chemical structure is shown below.

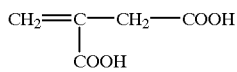

Itaconic acid is also called methylene succinic acid. It contains a propene functional group and two carboxylic acid reactive end groups. It is an active chemical species used to produce various polymers of different sizes. The products of polymerization can be used as the raw materials in producing plastics, rubbers, synthetic fibers, synthetic resins, surface active agents, ion exchangers, boiler detergents, glass fibers, lubricant supplements and so on. The market demand for itaconic acid is growing. However, the production technology for itaconic acid is held by a few companies and this information is seldom published. Therefore knowledge about the biosynthesis of itaconic acid and the regulation mechanism is limited.

BACKGROUND OF THE PRIOR ART

K. Kinoshita published a method for producing itaconic acid using Aspergillus itaconicus in 1931 in Bot.Mag., volume 45, pages 45–61. C. T. Calam et al. published a method for producing itaconic acid using Aspergillus terreus in 1939 in Biochem. J., volume 33, pages 1488–1495. T. Kobayashi and a colleague obtained Japanese patent in 1957 and in 1959 for the production of itaconic acid using Aspergillus itaconicus and Aspergillus terreus, with molasses used as the material to be fermented. K. Kinoshita obtained a similar patent in 1961 in the U.K. But these methods of itaconic acid production have not been used in industrial manufacturing. L. B. Lockwood published, on pages 455–469 of volume 6 of the Arch. Biochem. in 1945, a paper regarding the isolation of a new strain of Aspergillus terreus from soil for the production of itaconic acid. In the same year, A. J. Moyer et al. published, on pages 167–183, in volume 7 of Arch. Biochem., about the isolation of Aspergillus terreus from the soil. The former strain is suitable for either submerged or surface cultures, while the latter is better for surface cultures. In addition to Aspergillus, T. Tabuchi et al. published, in 1981, on pages 156–163 of colume 12 of Agric. Biol. Chem., a method using Candida and Rhdotorula yeast to produce itaconic acid. Currently industry is interested in using Aspergillus terreus to produce itaconic acid. The main cultivation methods in use are the submerged culture and the surface culture. N. Ju et al. published in 1986 on pages 311–314, in volume 23 of Appl. Microbiol. Biochem. regarding the use of porous stainless steel wire net for immobilizing fungus. This was then used for the continuous production of itaconic acid. H. Kautola et al. published in 1989 on pages 313–318, of volume 11, of the Biotechnol. Lett. a method of immobilizing fungus on polyurethane foam to produce itaconic acid using a continuous fermentation method. However, the previously mentioned immobilized fungus methods still haven't reached a practical mass production level. Although industry already successfully uses solid state fermentation for the production of citric acid and many other products, solid state fermentation for itaconic acid production has not been reported yet.

SUMMARY OF THE INVENTION

Figure 1:
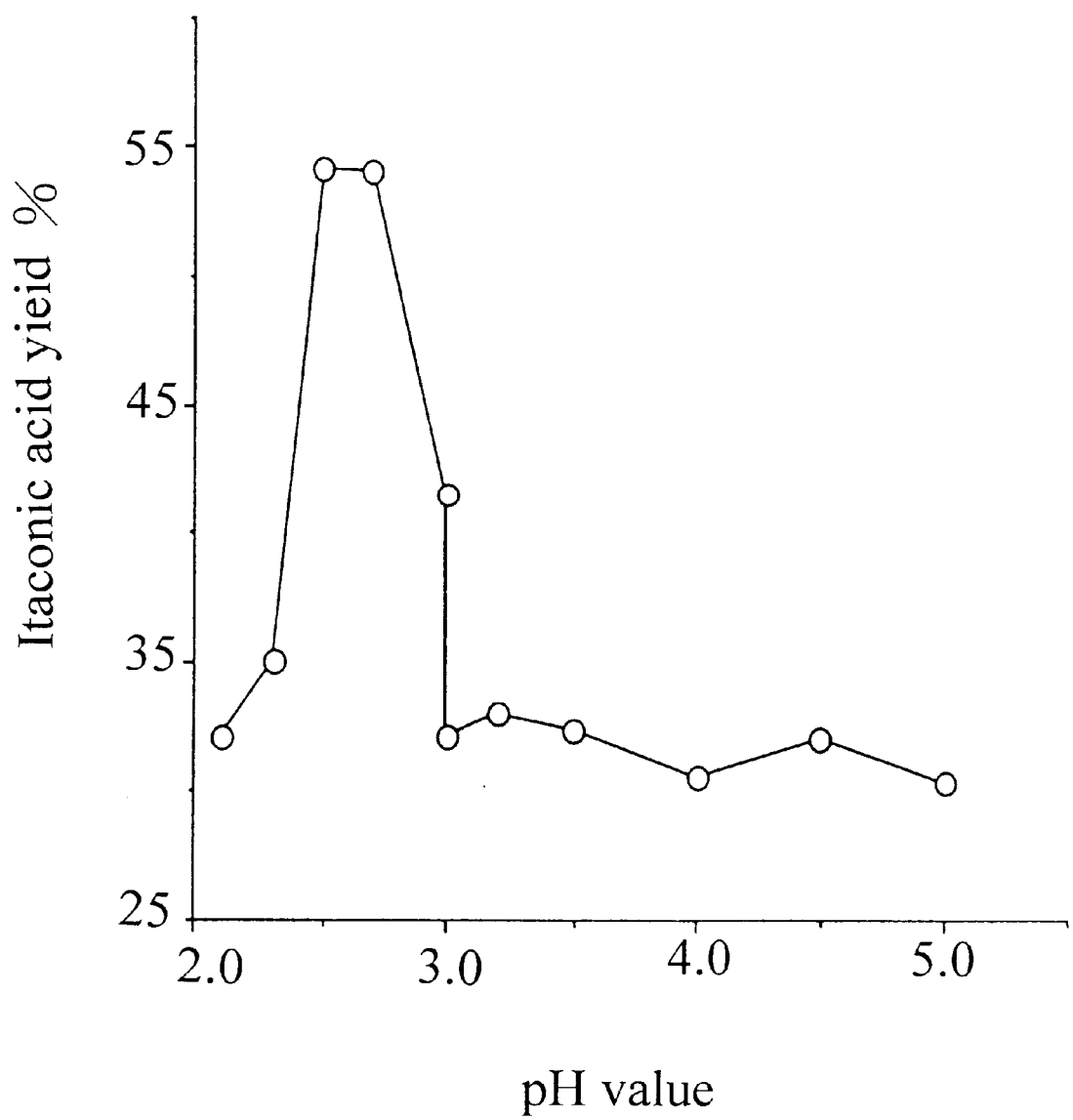
FIG. 1. Effect of initial medium pH on the percent yield of itaconic acid

This application describes a method for the production of itaconic acid by Aspergillus terreus using solid state fermentation. This method differs from previously reported methods. It is significant for the following reasons:

1) This method is the first method for a solid state fermentation production of itaconic acid. This method has the same advantages as those of common solid-state fermentations. These include lower cost of equipment, convenient recycling, noncomplexity of the fermentation manufacturing technology, especially in areas with unstable electrical supply. In addition, a solid-state fermentation method for producing citric acid is already being used in industry. This would make a facility and technology transition relatively easy.

2) This solid state fermentation method does not utilize starch as the material to ferment. This is significant because Aspergillus terreus does not have the ability to degrade starch in acidic condition. This method used sugarcane pressmud to adsorb liquid medium which contained suitable monosaccharides or disaccharides. The unpeeled sugarcane pressmud can adsorb 4 to 6 times its dry weight of medium. The peeled sugarcane pressmud can adsorb 8 to 14 times its dry weight of medium. At these adsorption levels additional liquid will not appear on the surface of the support. The characteristics of a solid-state fermentation can be maintained with good oxygen movement.

The important factors of this method for producing itaconic acid are as follows:
1) Fungal strain:
  It doesn't matter whether the strain of Aspergillus terreus is obtained from the individual strain maintenance center or isolated from the soil. Both can be treated to obtain high yield mutant strain. This method produced the M-8 strain from the ATCC 10020 strain by successive mutagenesis treatment using traditional mutagenesis methods, such as UV-irradiation, 1-methyl-3-nitro-nitrosoguanidine, and ethylmethanesulfonate. The M-8 strain achieves a 55% itaconic acid yield. Yield is defined as Yield (%)=itaconic acid production (g/g of medium)/initial medium total sugar content (g/g of medium)×100%.

2) Medium support:

The use of unpeeled or peeled sugarcane pressmud as support enables high levels of oxygen to be in and moving through the system easily at all times. The unpeeled sugarcane pressmud used in this method is pressmud produced from common sugarcane by squeezing out its juice. And the peeled sugarcane pressmud is produced from the peeled sugarcane by squeezing out its juice. Because unpeeled sugarcane pressmud contains peel, it is harder and its water holding capability is about 5–6 g/g dry weight. The water holding capability of peeled sugarcane pressmud is 14–16 grams/gram dry weight. The itaconic acid yield can reach 44–45% when using unpeeled sugarcane pressmud as a support and 50–55% when using peeled sugarcane pressmud as support. Fermentation time for the former is about 24 hours longer than that for the latter.

The water holding capability here means the amount of water adsorbed after the followed procedures are performed. The sugarcane pressmud must be dried to constant weight at 90 degree centigrade. Then the pressmud is immersed in water for 20 minutes.

The pressmud is removed from water and put in a centrifuge at 1500 g for 30 minutes. The adsorbed water was measured by substracting the dry pressmud weight from the weight of water saturated pressmud.

3) Carbon source:

The carbon sources used are glucose, sucrose, fructose, mannose, starch hydrolysate and molasses. Glucose, starch hydrolysate and sucrose are the best carbon sources for itaconic acid production. For example, the highest itaconic acid yield can be reached by adding 33% (w/v) starch hydrolysate solution to the medium. The starch hydrolysate used contains 30% w/v sugar as the carbon source.

4) Nitrogen source:

Non-organic nitrogen compounds such as ammonium sulfate, or ammonium nitrate can be used as the nitrogen source in the method. If ammonium sulfate is used as the nitrogen source, 0.2–0.4% (w/v in medium) are adequate concentrations.

5) pH value of medium:

The best initial pH value of the medium is between 2.0–3.0. FIG. 1 shows the yield of itaconic acid by M-8 mutant strain with peeled sugarcane pressmud as support and 10% glucose as carbon source under various initial pH conditions. From FIG. 1, we can see that the yield is highest when the initial pH values are between 2.5 and 2.8. The yield decreased dramatically when the pH values were higher than 3.0 or lower than 2.3.

6) Salt:

Adding a certain amount of salt into the solid-state medium during the fermentation process can improve the production rate of itaconic acid. Remarkable effectiveness can be reached by adding 22–500 mg of monobasic potassium phosphate, magnesium sulfate, calcium sulfate, zinc sulfate, ferric chloride, and copper sulfate.

The methods of analysis used to measure itaconic acid level were the methods of bromination method and HPLC analysis.

1) Bromination method a) Produce bromine using following reaction

6KBr+6HC →3Br$_2$+6 KCl+3 H$_2$O b) Use a measured amount of bromine to react with the itaconic acid CH$_2$C(COOH)CH$_2$COOH+Br$_2$→BrCH$_2$C(COOH)BrCH$_2$COOH c) Then use potassium iodide to react with the remaining bromine to produce potassium bromide and iodine Br$_2$+KI→2KBr+I$_2$ d) Finally use 0.1 N sodium thiosulfate to titrate the iodine I$_2$+2Na$_2$S$_2$O$_3$→Na$_2$S$_4$O$_6$+2 NaI The moles of iodine calculated will be equivalent to the moles of bromine left over after the reaction with itaconic acid. So if one subtracts the moles of bromine left over from the initial level one has the moles of bromine that reacted with the itaconic acid product. Since there is a one to one mole ratio in the stoichimetry of the reaction one can extrapolate the mole of itaconic acid produced.

Add 0.1 ml tested sample and 2 ml of 4.5% HCl into a 25 ml capped bottle, then incubate under 30 degree centigrade for 30 minutes. Add 0.5 ml of 30% potassium bromide, incubate again at 30 degree centigrade for 10 minutes, react the KI to completion with Br$_2$, and then titrate with sodium thiosulfate using starch as indicator.

2) HPLC method

The column used for HPLC analysis of itaconic acid was LiChroCART(5-mm particle size, 125-mm length, 4-mm diameter, E. Merck, Germany). The elution buffer contained 2.5 mM NaH$_2$PO$_4$ and 2.5 mM Na$_2$HPO$_4$, and the pH was adjusted to 3.0 with H$_2$SO$_4$. The column was eluted with a flow rate of 1 ml/min at room temperature. Itaconic acid was detected at 200 nm with a Waters 484 Absorbance Detector (Millipore Corporation, USA). Samples were filtered through a 0.2 mm pore-size membrane before analysing.

The strain of *Aspergillus terreus* M8 has been sent to American Type Culture Collection (ATCC) located at 10801 University Blvd., Manassas, Va. 20110-2209, deposit received Mar. 8, 2000, which has issued Patent Deposit Designation No. PTA-1467.

EXAMPLE 1

Itaconic acid solid-state fermentation process with peeled sugarcane pressmud as support and glucose as carbon source.

Figure 2:
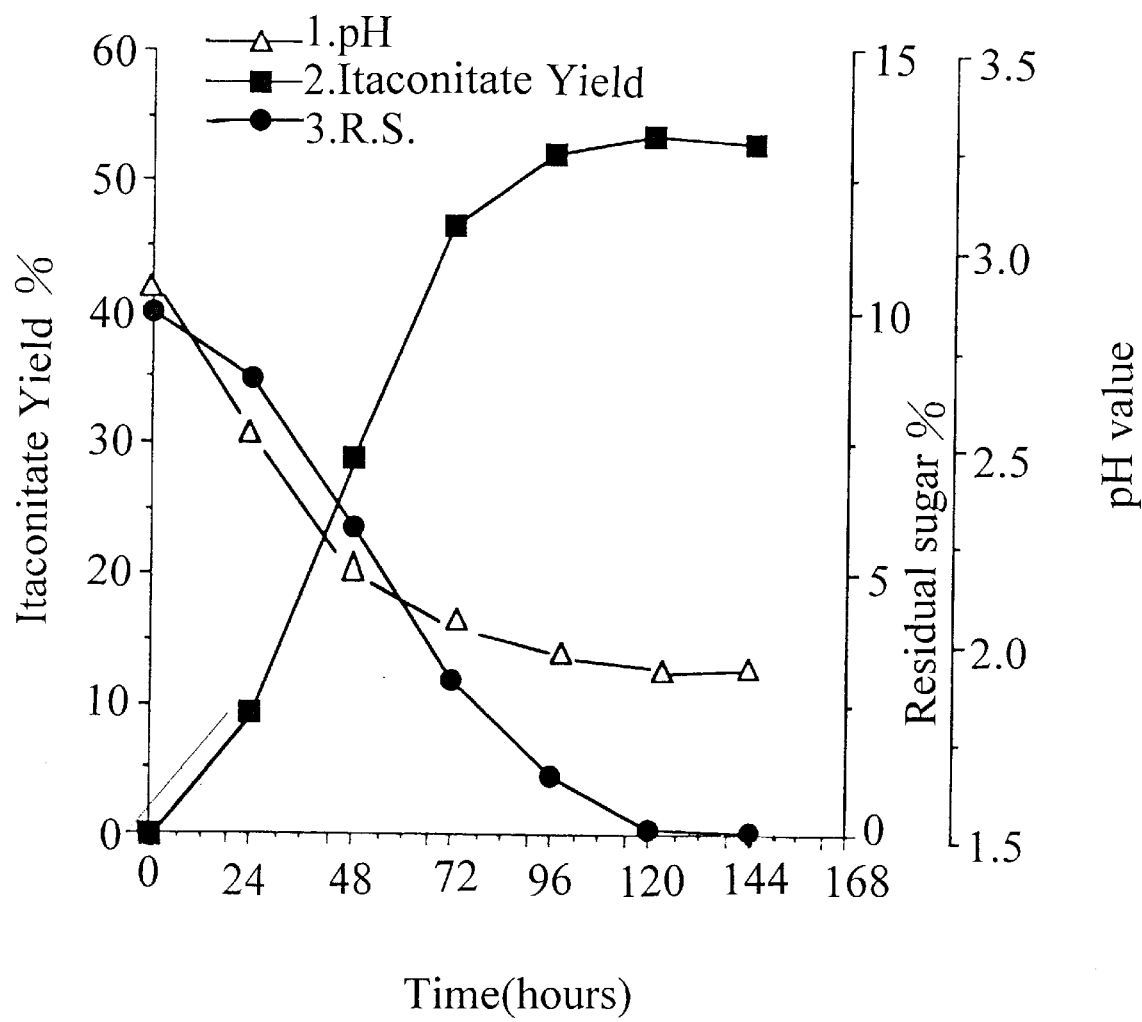
FIG. 2. Time course of itaconic acid fermentation with peeled sugarcane pressmud as support
  1. pH value
  2. percent yield of itaconic acid based on initial sugar content
  3. residual sugar content FIG. 3. Time course of itaconic acid fermentation with washed unpeeled surgarcane pressmud as support
  1. pH value
  2. percent yield of itaconic acid based on initial sugar content
  3. residual sugar content

A 5 g sample of washed and dried peeled sugarcane pressmud was rehydrated in 250-ml flask with 45 ml of medium A. After autoclaving at 121 degree centigrade for 20 minutes, 0.5 ml of spore suspension (1×10$^7$ spores/ml) of A. Terreus M8 strain was added, and then the flask was incubated at 35 degree centigrade for 4 days. FIG. 2 demonstrates the time course of fermentation. The yield of itaconic acid based on the initial sugar content of the medium reached 55%. (w/v). The glucose was totally consumed by the fifth day. The pH value decreased from the initial 2.7 to approximately 2.0.

| MEDIUM A | |
|---|---|
| glucose | 100 g |
| (NH$_4$)$_2$SO$_4$ | 3 g |
| KH$_2$PO$_4$ | 0.1 g |
| MgSO$_4$.7H$_2$O | 0.5 g |
| CaSO$_4$.2H$_2$O | 0.4 g |
| ZnSO$_4$.7H$_2$O | 0.5 mg |
| FeCl$_3$ | 3.0 mg |
| CuSO$_4$ | 0.5 mg |
| water to 1000 ml | pH 2.3 |

EXAMPLE 2

Itaconic acid solid-state fermentation process with peeled sugarcane pressmud as support and starch hydrolysate as carbon source.

The conditions used here are identical to those used in Example 1, except that the glucose(10%) w/v in medium A was replaced by 33% w/v starch hydrolysate which contained 30% w/v total sugar. The yield of itaconic acid based on the initial sugar content of medium reached 55% w/w.

EXAMPLE 3

Itaconic acid solid-state fermentation process with unwashed peeled sugarcane pressmud as support and starch hydrolysate as carbon source.

The conditions used here are identical to those used in Example 1, except that unwashed peeled sugarcane pressmud was used instead of washed pressmud and the glucose(10%) in medium A was replaced by 27% starch hydrolysate which contained 30% total sugar. Since the unwashed pressmud contained 17% sugar, the initial sugar content of the medium of Example 3 was the same as that of Example 1 and 2. The yield of itaconic acid based on the initial sugar content of medium reached to 50%.

EXAMPLE 4

Figure 3:
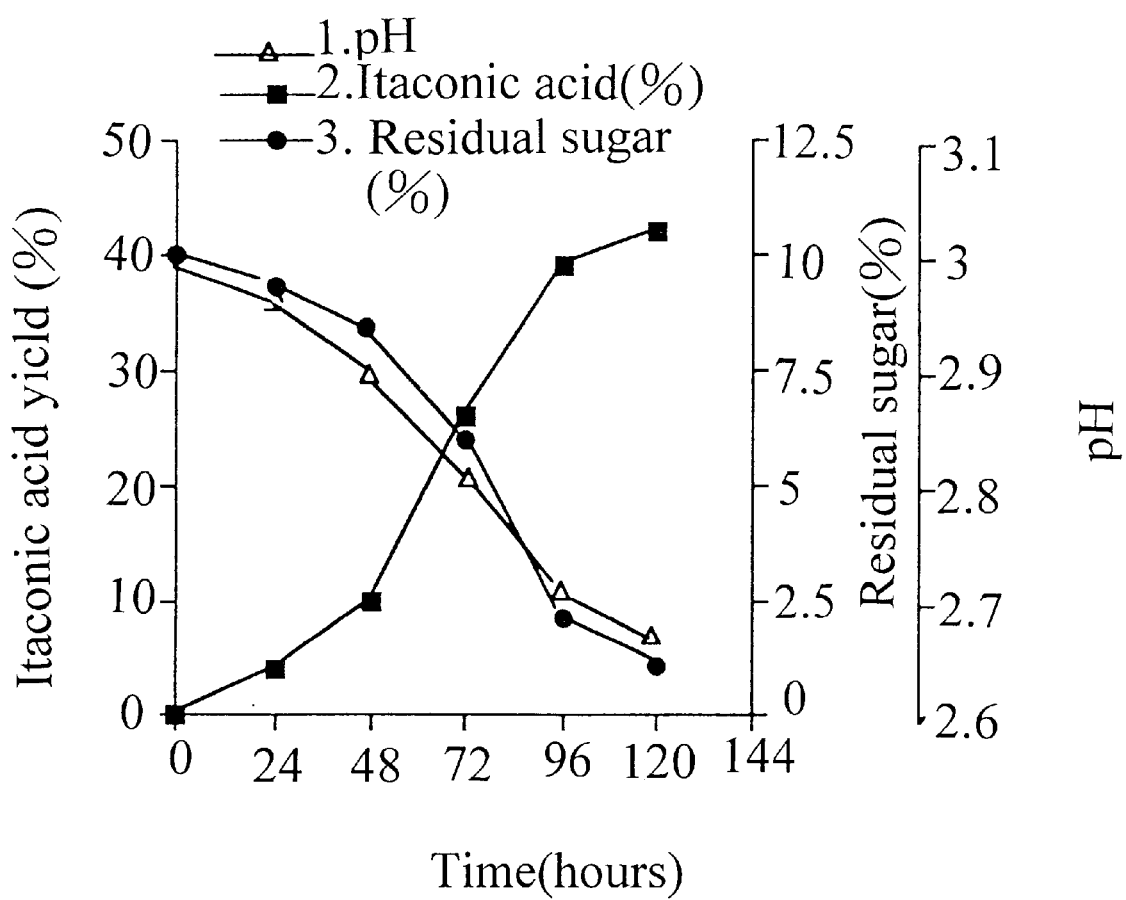

Itaconic acid solid-state fermentation process with washed unpeeled sugarcane pressmud as support and starch hydolysate as carbon source A 10 g sample of washed and dried unpeeled sugarcane pressmud was rehydrated in 250-ml flask with 40 ml of medium B, which has the same composition of medium A except that the glucose concentration is 12% instead of 10%. The other conditions used are identical to those used in Example 1. FIG. 3 demonstrates the time course of fermentation. The yield of itaconic acid based on the initial sugar content of the medium reached 42%.

What is claimed is:

1. A method of producing itaconic acid which consists of the steps of:

1) subjecting dried and peeled sugarcane pressmud to rehydration with a medium consisting of glucose 100 g; $(NH_4)_2SO_4$ 3 g; $KH_2PO_4$ 0.1 g; $MgSO_4.7H_2O$ 0.5 g; $CaSO_4.2H_2O$ 0.4 g; $ZnSO_4.7H_2O$ 0.5 mg; $FeCl_3$ 3.0 mg; $CuSO_4$ 0.5 mg; water to 1000 ml to obtain a rehydrated pressmud;

2) autoclaving at 121° for 20 minutes for rehydrated pressmud from step 1);

3) subjecting the autoclaved pressmud from step 2) to a solid state fermentation with the strain *Aspergillus terreus* M8 and incubating at 35° C. for four days while the pH decreases from 2.7 to 2;

4) and recovering itaconic acid.

* * * * *